United States Patent [19]
Komatsu et al.

[11] Patent Number: 5,537,202
[45] Date of Patent: Jul. 16, 1996

[54] POWDER SAMPLE FORMING APPARATUS

[75] Inventors: Takashi Komatsu; Hiroomi Uehara; Syuji Shinkai, all of Iruma-gun, Japan

[73] Assignee: Japanese Research And Development, Association For Intelligent Control System In The Food Industry, Tokyo, Japan

[21] Appl. No.: 350,774

[22] Filed: Dec. 7, 1994

[30] Foreign Application Priority Data

Jul. 12, 1993 [JP] Japan .................................. 5-340002

[51] Int. Cl.⁶ .................................................. G01N 1/00
[52] U.S. Cl. ..................... 356/36; 73/864.31; 73/864.81; 250/358.1
[58] Field of Search ..................... 356/36, 244, 445–448, 356/243, 418, 241, 338; 73/864.31, 864.81, 863.43, 863.32; 250/574, 338.1, 339.07, 358.1

[56] References Cited

U.S. PATENT DOCUMENTS

| | | |
|---|---|---|
| 3,224,324 | 12/1965 | Coppock et al. . |
| 3,328,587 | 6/1967 | Brown et al. . |
| 3,575,055 | 4/1971 | Thornton, Jr. . |
| 3,869,213 | 3/1975 | Greene ..................... 356/244 |
| 4,040,747 | 9/1977 | Webster ..................... 356/243 |
| 4,154,533 | 5/1979 | Levine ....................... 356/445 |
| 4,478,094 | 10/1984 | Salomaa et al. . |
| 4,479,055 | 10/1984 | Perten . |
| 4,538,908 | 9/1985 | Webster ..................... 356/36 |
| 4,640,614 | 2/1987 | Roberts et al. ........... 356/36 |
| 4,793,326 | 12/1988 | Shishido ................... 356/241 |
| 5,087,120 | 2/1992 | Anthony ................... 356/36 |

*Primary Examiner*—K. Hantis
*Attorney, Agent, or Firm*—Townsend and Townsend and Crew

[57] ABSTRACT

A powder sample forming apparatus includes: a guide table horizontally secured on a mounting table; an upper fixed board which is fixed to the guide table and arranged in parallel with the guide table with a certain distance apart above the guide table and has a transparent plate for metering in its approximate center; a slide block having a through-hole for holding a sample in its one end and disposed between the guide table and the upper fixed board so as to move back and forth within a sliding distance longer than the length of the upper fixed board; and a sample pressing device which is disposed under the guide table in a position of the transparent plate and presses a sample from the underside of the transparent plate.

12 Claims, 4 Drawing Sheets

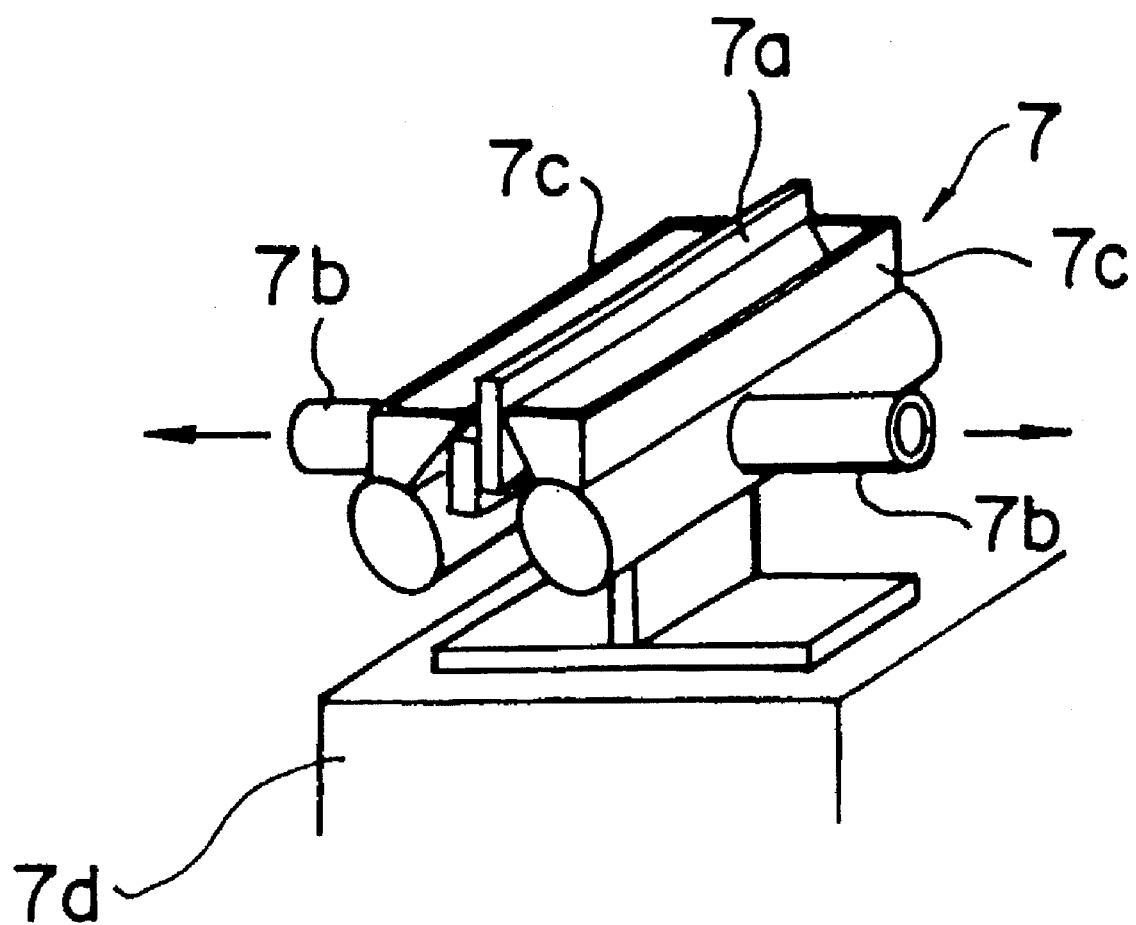
F I G. 2

POWDER SAMPLE FORMING APPARATUS

BACKGROUND OF THE INVENTION

1. Field of the Invention

The present invention relates to a powder sample forming apparatus.

2. Description of the Prior Art

There are several kinds of apparatuses for analyzing powder materials such as a spectral analyzer, hue-meter etc., in which a powder material such as wheat flour is analyzed for determining the nature of the material by illuminating the powder material and receiving the reflected or transmitted light for measurement. One of critical factors for the measurement is to make uniform the surface state of the powder to be measured. This operation is called as forming a powder sample.

Conventionally, when a powder sample to be used for the spectral metering is formed, in order to cause the surface state of the powder to become uniform, the powder sample is loaded into a cell, i.e., a shallow dish type container having a glass window on its bottom side and then the upper side of the powder is leveled off by scraping operation. The thus flattened powder surface is pressed against the cell bottom so that the portion of the powder material abutting the glass window, that is, the surface to be examined, may become uniform. Since any of these steps is operated manually, personal differences may occur depending upon the operators, and in some cases, the surface state of the sample may be made different in each measurement, thus the result would involve measurement errors. Further, even though the spectral measurement could be automated, it has been still difficult up to now to convert the whole operations into an automatic system.

SUMMARY OF THE INVENTION

The present invention has been achieved in view of what is described above and it is an object of the present invention to provide a powder sample forming apparatus in which the entire operations from the loading of a powder sample to the discharge of the powder sample are automatically carried out.

In order to achieve the above object, a powder sample forming apparatus of the present invention includes: a guide table horizontally secured on a mounting table; an upper fixed board fixed to the guide table and arranged in parallel with the guide table with a certain distance apart above the guide table; a slide block slidably disposed between the guide table and the upper fixed board; a spectral apparatus disposed over the upper fixed board; a sample pressing device fixed under the guide table; and a discharging device for discharging a powder sample from the slide block. Further, the powder sample forming apparatus is constructed such that the slide block has a through-hole for receiving a powder sample near one end thereof, a correcting device for adjusting the spectral apparatus fixed on the top face near the other end thereof and a glass cleaning device built inside in the middle portion thereof, the upper fixed board has a leveling blade disposed so as to come in sliding contact with the top face of the slide block and a glass plate transmitting light emitted from the spectral apparatus. In the powder sample forming apparatus, the sample pressing device projects into the slide block through the guide table so as to press a powder sample against the glass plate at the time of metering while the glass cleaning device rises during the movement of the slide block so as to wipe the undersurface of the glass plate.

At the time of loading a sample, the slide block that slides on the guide table is set so that the through-hole is positioned near the end on the guide table. In this state, when a powder sample is supplied by a proper means, the through-hole in the slide block bottomed with the guide table is filled with the powder sample to form a raised heap of the powder above the brim. When the slide block thus filled with the sample is shifted toward the center, the leveling blade disposed on the edge of the upper fixed board scrapes the top heap of the powder raised above the brim of the through-hole. When the slide block further advances until the sample powder containing portion (the through-hole) reaches a place under the transparent plate (a glass plate in the embodiment herein) provided in the center of the upper fixed board and stops there. As a pressing piston disposed under the guide table rises, a plate attached on the top end of the piston and having a substantially similar dimension to that of the through-hole is pushed up so as to press the sample powder loaded against the transparent plate. Therefore, it is possible to change the degree of pressing by adjusting the stroking distance of the piston. In this state, the surface of the powder thus made even is illuminated over the transparent plate and the reflected light or the like is metered.

When the measurement is complete, the pressing plate goes down to the level of the slide table, and then the slide block is reversed to its initial position and is further moved in that direction until the through-hole clears the edge of the slide table. This travel allows the sample powder loaded in the through-hole to discharge outside. At that time, an air blower or a piston etc. may be used to discharge the powder, so that the inside of the through-hole is cleaned as required. After the discharge and cleaning, the slide block is returned once to the initial position for waiting a next sample loading. Thus, one cycle consisting of sample loading, sample pressing for smoothing metered surfaces, and sample discharge and cleaning can be effected by only sliding the slide block. Further, if a brush, a cleaner and a sucking tube for cleaning the dirtiness caused by pressing a powder sample on the transparent plate disposed in the upper fixed board are equipped in a center portion of the slide block apart from the place of the through-hole, it is possible to clean the metering window in every stroke, thus making it possible to reduce measurement errors.

Metering apparatuses of this kind (such as of a whiteness-meter, for example) need correction of measured data using a reference plate in order to obtain proper measurement. To deal with this, the reference plate may be placed on the top face of the slide block around the opposite end portion to the powder containing portion (the through-hole). With this configuration, when the slide block moves for sample loading, the reference plate comes to the right place for metering (the place where the transparent plate is disposed), so that the correction of the metering apparatus can be made simultaneously with the operation of sample loading. Therefore, each component is positioned in place in the slide block. More specifically, the reference plate, for example, may be positioned so that it comes to the metering portion at the time of powder discharge (when the slide block is moved to the most distance position) while the cleaning device in the slide block may be positioned so as to occupy the metering portion when the slide block is returned to some extent from the most distance position to allow sample loading. In the powder sample forming apparatus thus configurated, it is possible to effect window cleaning and correction of metering as the slide block repeatedly moves for sample loading, metering and discharging.

Although batch operation or successive operations may be done for loading powder material into the sample containing portion, in either case, the powder material must be heaped above the brim of the containing portion. The vertical section of the containing portion is preferably a trapezoid having an upper side shorter than a lower side. There is no particular limitation on the transversal section of the containing portion, but it is preferable to form it in a circular shape in view of allowing the piston to smoothly operate and reducing residual powder adhered. Although a glass plate is used for the transparent plate in the embodiment of the present invention, a plate made of plastic can be used instead.

BRIEF DESCRIPTION OF THE DRAWINGS

FIG. 2 is a perspective view showing a glass cleaning device used in the powder sample forming apparatus of the present invention;

DETAILED DESCRIPTION OF PREFERRED EMBODIMENT

Now, a powder sample forming apparatus of the present invention will be described with reference to the accompanying drawings.

Figure 1:
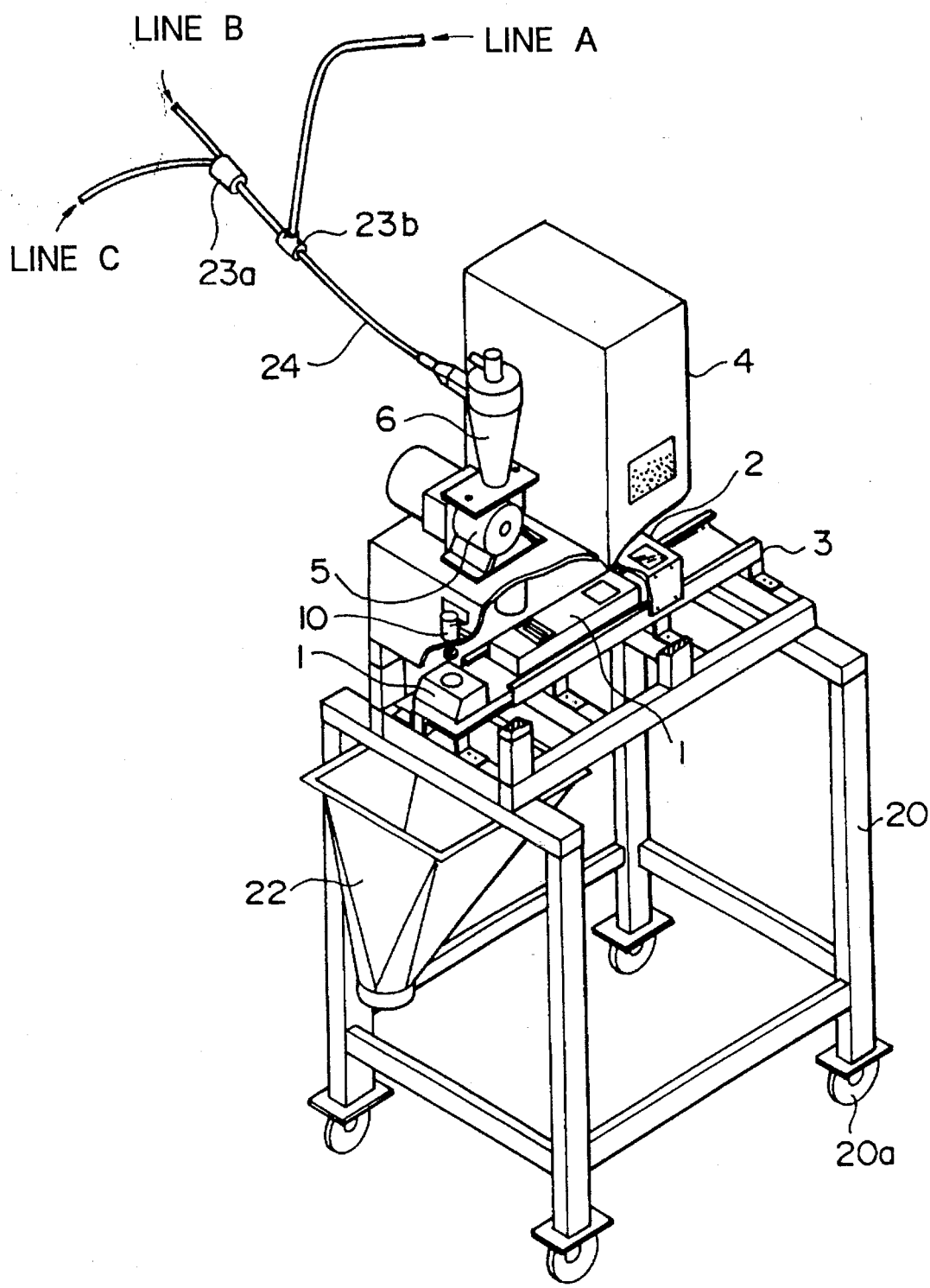
FIG. 1 is a perspective view showing a powder sample forming apparatus of the present invention.

FIG. 1 is a perspective view showing a powder sample forming apparatus of the present invention.

Main components of the powder sample forming apparatus of the present invention are provided on a mounting table 20 under which casters 20a are attached. The main components include: a guide table 3 secured on the mounting table 20; an upper fixed board 2 fixedly arranged in parallel with the guide table 3 with a certain distance apart above the guide table 3; a slide block disposed between the guide table 3 and the upper fixed board 2 so as to move back and forth; a sample pressing device 8 disposed under the guide table 3; a glass cleaning device 7 provided inside the slide block 1; a spectral apparatus 4 arranged above the upper fixed board 2; and a locker 5.

The guide table 3 is mainly composed of a horizontal board on which the slide block 1 is slidably supported and has a through-hole 3a therein. The aforementioned sample pressing device 8a, which is composed of a cylinder 8a and a piston, is arranged vertically inside the through-hole 3a. The cylinder 8a is fixed to the mounting table 20 while the piston 8b is provided so as to be able to rise through the hole 3a.

A glass plate 2a is fixed to a through-hole 2c which is provided in a substantial center of the upper fixed board 2. A pair of leveling blades 2b made of hard rubber are attached in the front edge (on the left side in the figure) of the upper fixed board 2. These leveling blades 2b are so arranged that the lower edges thereof come in sliding contact with the upper face of the slide block 1.

The slide block 1 is adapted to move back and forth in a horizontal direction relative to the mounting table 20 by means of a rack and pinion gear mechanism, a screw sliding mechanism, a hydraulic mechanism or any other such device. The slide block 1 has a through-hole 1a near the front end (on the left side in the figure) for holding a powder sample P and another through-hole 1b in a substantially central part thereof. Provided inside the through-hole 1b is the glass cleaning device 7. Further, a correcting device 9 is attached on the upper surface near the right end of the slide block 1. This correcting device 9 is to present a reference for normalizing the spectrum of the spectral apparatus 4. Besides, there is a discharging hopper 22 under the slide block 1.

FIG. 2 is a perspective view of the glass cleaning device.

As shown in FIG. 2, the glass cleaning device 7 is composed of a glass cleaning part and a piston/cylinder 7d. The glass cleaning part has an elongated scraper 7a made of hard rubber and a pair of vessels 7c disposed so as to pinch the scraper on both sides. A vacuum sucking pipe 7b is connected to these vessels 7c. The cylinder part of the piston-cylinder 7d is secured to the slide block 1 while the piston part causes the glass cleaning part to move up and down so that the scraper 7a comes near to the upper fixed board 2 and retracts therefrom. The scraper 7a is so arranged that the length thereof may be perpendicular to a moving direction of the upper fixed board 2.

The spectral apparatus 4 and the locker 5 are of publicly known configurations, and the locker 5 is connected to a cyclone 6 which in turn is connected with production lines A, B, C etc. by way of a powder transporting tube 24 and a change-over valve 23a.

Next, the operation of the powder sample regulating apparatus of the present invention will be described with reference to the drawings.

Figure 3:
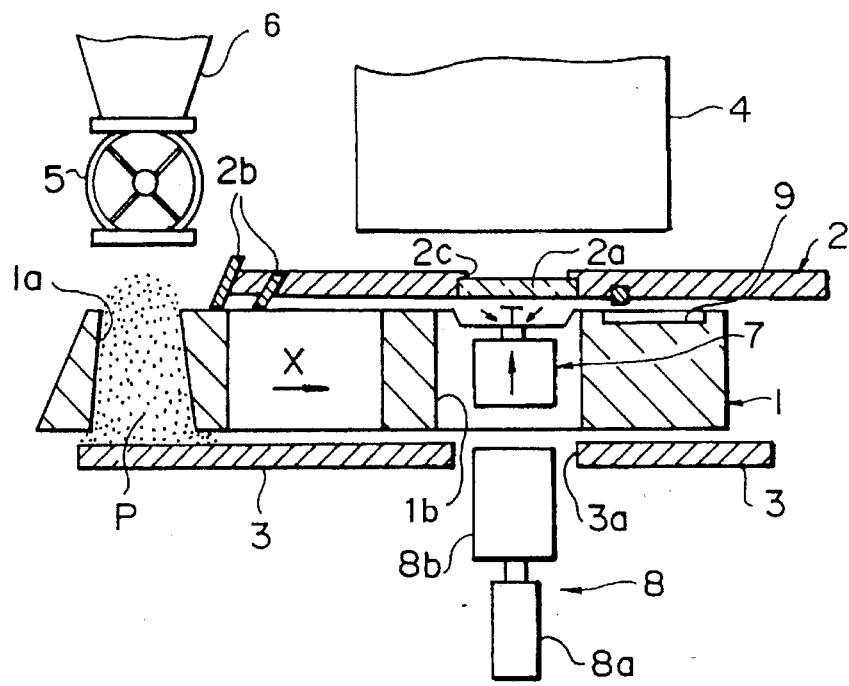
FIG. 3 is a view illustrating a powder loading operation in the powder sample forming apparatus of the present invention.
Figure 4:
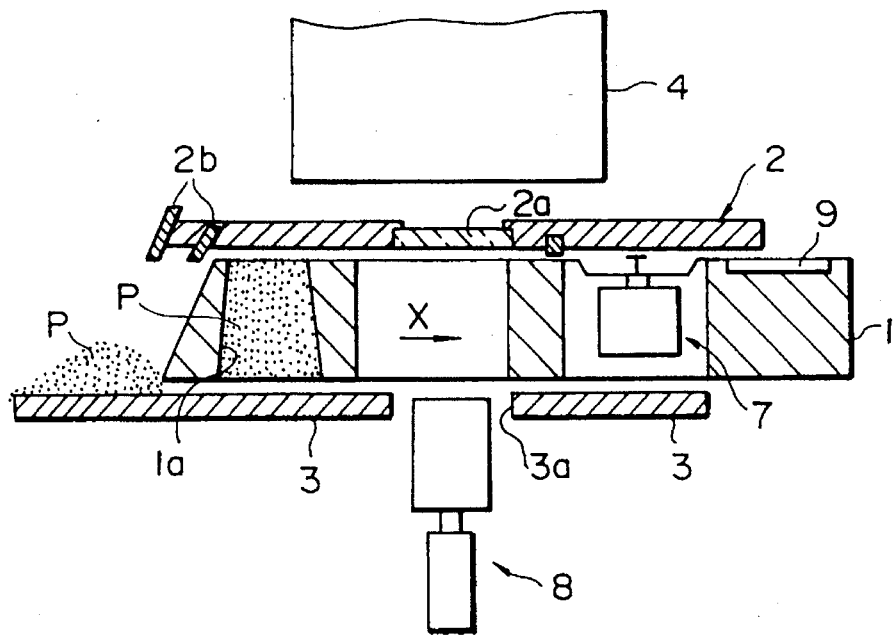
FIG. 4 is a view illustrating a leveling operation effected in the apparatus of the present invention.
Figure 5:
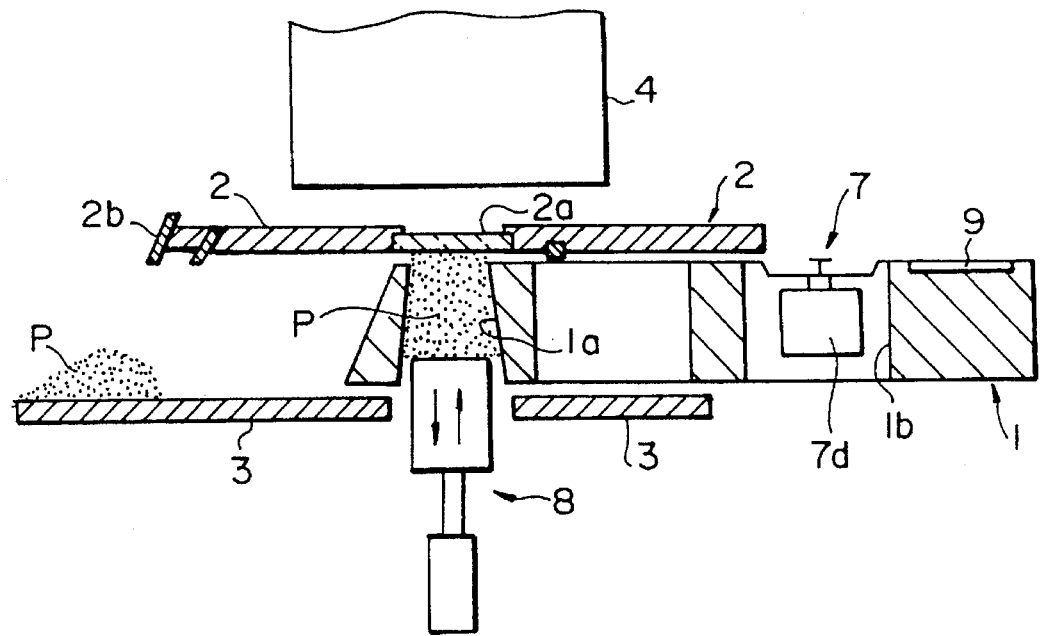
FIG. 5 is a view illustrating a metering operation in the apparatus of the present invention.
Figure 6:
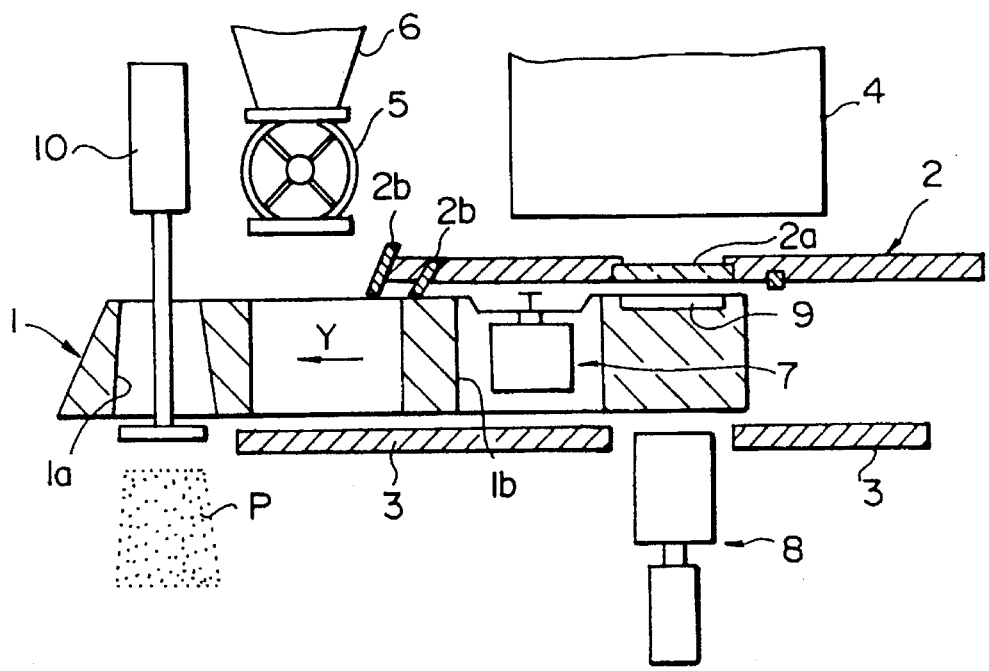
FIG. 6 is a view illustrating a discharging operation in the apparatus of the present invention.

FIGS. 3 through 6 are views showing operations in a sequence of the powder sample regulating apparatus of the present invention. Specifically, FIG. 3 shows a powder loading operation, FIG. 4 shows a leveling operation, FIG. 5 shows a metering operation and FIG. 6 shows a discharging operation.

As shown in the powder loading operation in FIG. 3, an arbitrary sample P from any one of powder production lines A, B, C etc., selected by the change-over valve 23a is collected into the cyclone 6 by means of a vacuum sucking device. The rotation of the locker 5 allows the thus collected powder sample P to be supplied into the hollow defined by the hole 1a of the slide block 1 and the top surface of the guide table 3 until the powder brims over. In this while, the slide block 1 stays still. Then the slide block 1 is moved in X-direction (toward the right in the figure). During the movement, the glass cleaning device 7 is activated so that the scraper 7a wipes the undersurface of the glass plate 2a of the upper fixed board 2 to clean it. As a result, powder particles adhered on the under face of the glass plate 2a is scraped off and falls into vessels 7c. The thus collected powder is discharged by the sucking function of the vacuum sucking pipe 7b. This glass cleaning device 7 is constructed so as to be made active only while passing under the glass plate 2a of the upper fixed board 2.

As shown in the leveling operation in FIG. 4, when the hole 1a of the slide block 1 passes under the leveling blades 2b of the top fixed board 2, the flowing powder sample P over the brim of the hole 1a of the slide block 1 is leveled on its upper face by the leveling blades 2b. Here, a pair of leveling blades 2b are used, but the number of the blades is not limited to singularity or plurality.

As shown in the metering operation in FIG. 5, the slide block 1 moves until the hole 1a of the slide block 1 reaches the position under the glass plate 2a of the upper fixed board 2 and stops there. Then, the sample pressing device 8 is activated so that the piston 8b rises and presses the powder sample P up against the undersurface of the glass plate 2a. In this configuration, a flexible rubber or cloth is preferably attached on the top of the piston 8b. The upper surface of the thus compressed powder sample P is illuminated by the spectral apparatus 4 and the reflected or transmitted light is metered whereby the nature of the powder is analyzed. After the measurement, the piston 8b descends, then the slide block 1 starts to move in Y-direction. In the course of this movement, the glass cleaning device 7 is activated so as to clean the undersurface of the glass plate 2a while the device 7 passes under the glass plate 2a of the upper fixed board 2. In this way, the glass plate 2a can be cleaned twice in one reciprocating travel of the slide block 1.

As shown in the discharging operation in FIG. 6, the slide block 1 halts at the time the block 1 arrives under the glass plate 2a of the upper fixed board 2, in order to readjust the spectrum of the light emitted from the spectral apparatus 4 to the reference using the correcting device. At the time, the hole 1a of the slide block 1 is located right under the discharging device 10, which, by means of an electric device, hydraulic device etc., descends to push out the powder sample P inside the hole 1a into the discharging hopper 22. Thus, one cycle of the operations is complete.

The aforementioned whole operations, specifically, the back and forth movement of the slide block 1, the sample supply, the up and down movement of the glass cleaning device 7, the up and down movement of the sample pressing device 8, the operation of the spectral apparatus 4, the up and down movement of the discharging device 10 and the timing control for the operations of these components are all automatically carried out.

Although the foregoing embodiment of the powder sample regulating apparatus of the present invention has been described in conjunction with the use for spectral analyzing, it is possible to use the present invention to regulate samples for hue-meters and whiteness-meters of powder materials.

As has been described heretofore, in the apparatus of the present invention, a powder sample taken from any production line is fed by means of the locker into the hollow of the slide block, the upper face of the fed sample is flattened by leveling blades, and then the sample is pressed against the glass plate located right below the spectral apparatus so that the surface state of the powder sample is made uniform. The thus unformed powder sample is metered by means of the spectral apparatus, thereafter the measured powder sample is discharged. In this while, the measurement is corrected with the correcting device and the glass plate is cleaned for every operation in order to ensure purity of powder samples. As a result, it is possible to achieve excellent effects as follows.

(1) Since surface states of powder samples can be always formed in the same manner, it is possible to achieve exact measurement of powder samples using a spectral apparatus.

(2) The metering operation of a powder sample can be automatically performed, without any manual operation, from the feeding of the sample to the discharge.

(3) Various samples taken from powder producing plants, lines or processes can be collectively formed, analyzed etc. at the same place.

What is claimed is:
1. A powder sample forming apparatus comprising:

a guide table horizontally secured on a mounting table;

an upper fixed board fixed to said guide table and arranged in parallel with said guide table and spaced a distance above said guide table, said upper fixed board having a transparent plate for metering in an approximate center thereof;

a slide block having a through-hole for holding the sample in one end thereof and disposed between said guide table and said upper fixed board so as to move back and forth within a sliding distance longer than the length of said upper fixed board; and a sample pressing device which is disposed under said guide table in a position of said transparent plate and presses the sample from the underside of said transparent plate.

2. A powder sample forming apparatus according to claim 1 wherein said upper fixed board has a leveling blade in sliding contact with the top surface of said slide block.

3. A powder sample forming apparatus according to claim 1 wherein a correcting device for apparatus adjustment is provided on the top face of said slide block near the other end opposite to said through-hole.

4. A powder sample forming apparatus according to claim 3 wherein said slide block is arranged such that, when said through-hole in said slide block is positioned for supplying or discharging a sample, said correcting device occupies the place to be metered.

5. A powder sample forming apparatus according to claim 1 wherein said slide block further has a cleaning device for cleaning said transparent plate for metering.

6. A powder sample forming apparatus according to claim 5 wherein said cleaning device for cleaning the metering portion comprises a scraper and sucking nozzles on both sides of said scraper.

7. A powder sample forming apparatus comprising:

a guide table horizontally secured on a mounting table;

an upper fixed board fixed to said guide table and spaced a distance above said guide table, said upper fixed board having a transparent plate for metering in an approximate center thereof;

a slide block having a through-hole for holding the sample in one end thereof and disposed between said guide table and said upper fixed board so as to move back and forth within a sliding distance longer than the length of said upper fixed board; and a sample pressing device which is disposed under said guide table in a position of said transparent plate and presses the sample from the underside of said transparent plate, said upper fixed board further comprising a leveling blade disposed so as to come in sliding contact with the top face of said slide block, said slide block further comprising a correcting device for apparatus adjustment on the top face thereof near the other end opposite to said through-hole and a cleaning device disposed between the fixed board and the guide table for cleaning said transparent plate for metering.

8. A powder sample forming apparatus comprising:

a guide table horizontally secured on a mounting table;

an upper fixed board fixed to said guide table and arranged in parallel with said guide table and spaced a distance above said guide table;

a slide block slidably disposed between said guide table and said upper fixed board;

a spectral apparatus disposed over said upper fixed board;

a sample pressing device fixed under said guide table and a discharging device for discharging the powder sample from said slide block, said slide block having a through-hole for receiving the powder sample near one end thereof, a correcting device for adjusting said spectral apparatus fixed on the top face near the other end thereof and a glass cleaning device built inside in a middle portion thereof;

said upper fixed board having a leveling blade disposed so as to come in sliding contact with the top face of said slide block and a glass plate transmitting light emitted from said spectral apparatus; and wherein said sample pressing device projects into said slide block through said guide table so as to press the powder sample against said glass plate at the time of metering while said glass cleaning device rises during the movement of said slide block so as to wipe the undersurface of said glass plate.

9. A method for analyzing a powder sample comprising:

introducing the powder sample into a through-hole of a sliding block at a first position;

moving the sliding block in a substantially horizontal direction until the powder sample is disposed at a second position adjacent a spectral apparatus;

compressing the powder sample after the moving step; and analyzing the powder sample with the spectral apparatus.

10. The method of claim 9 further comprising leveling a top surface of the powder sample during the moving step.

11. The method of claim 9 further comprising cleaning a transparent plate during the moving step, the transparent plate being positioned between the spectral apparatus and the powder sample.

12. The method of claim 9 further comprising:

moving the slide block in a second direction opposite the first direction until the powder sample is in the second position; and discharging the powder sample from the through-hole of the slide block.

* * * * *